(12) United States Patent
Huang

(10) Patent No.: US 12,083,038 B2
(45) Date of Patent: Sep. 10, 2024

(54) DENTAL APPLIANCE

(71) Applicant: Steven Wen-Ku Huang, San Marino, CA (US)

(72) Inventor: Steven Wen-Ku Huang, San Marino, CA (US)

( * ) Notice: Subject to any disclaimer, the term of this patent is extended or adjusted under 35 U.S.C. 154(b) by 76 days.

(21) Appl. No.: 17/848,029

(22) Filed: Jun. 23, 2022

(65) Prior Publication Data

US 2022/0347005 A1 Nov. 3, 2022

Related U.S. Application Data

(63) Continuation of application No. 16/277,663, filed on Feb. 15, 2019, now Pat. No. 11,369,510.

(51) Int. Cl.
*A61F 5/00* (2006.01)
*A61F 5/56* (2006.01)
*A63B 71/08* (2006.01)
*A61C 7/08* (2006.01)

(52) U.S. Cl.
CPC ............ *A61F 5/566* (2013.01); *A63B 71/085* (2013.01); *A61C 7/08* (2013.01); *A61F 2005/563* (2013.01)

(58) Field of Classification Search
None
See application file for complete search history.

(56) References Cited

U.S. PATENT DOCUMENTS

| | | | |
|---|---|---|---|
| 3,518,988 A | 7/1970 | Gores | |
| 5,611,355 A | 3/1997 | Hilsen | |
| 5,823,193 A | 10/1998 | Singer | |
| 6,505,625 B1 | 1/2003 | Uenishi | |
| 7,607,438 B2 | 10/2009 | Pelerin | |
| 7,730,891 B2 | 6/2010 | Lamberg | |
| 7,840,042 B2 | 11/2010 | Kriveshko | |
| 8,166,976 B2 | 5/2012 | Webster | |
| 9,545,331 B2 | 1/2017 | Ingemarsson-Matzen | |
| 9,681,978 B1 | 6/2017 | Roth | |
| 10,952,821 B2 | 3/2021 | Falkel | |
| 11,369,510 B2 * | 6/2022 | Huang | ............ A61F 5/566 |
| 2006/0021622 A1 | 2/2006 | Buffington | |
| 2007/0079833 A1 | 4/2007 | Lamberg | |
| 2011/0195376 A1 | 8/2011 | Boyd | |

(Continued)

FOREIGN PATENT DOCUMENTS

CN 205514975 U 8/2016
DE 202004020196 U1 5/2005

(Continued)

OTHER PUBLICATIONS

KR 20180116089 A Translation (Year: 2018).*

(Continued)

*Primary Examiner* — Kim M Lewis

(74) *Attorney, Agent, or Firm* — Matthew J. Spark; Stefan J. Kirchanski; Zuber Lawler LLP

(57) ABSTRACT

A mouth guard includes a tray configured to encompass at least anterior teeth of a dental arch. The tray includes a pair of protrusions extending away from the tray, each protrusion configured to generally overlie a canine of the dental arch. The protrusions are configured to engage one or more anterior teeth of a dental arch, whereby damage to the at least anterior teeth of the dental arch is reduced or prevented.

14 Claims, 6 Drawing Sheets

(56) References Cited

U.S. PATENT DOCUMENTS

| | | |
|---|---|---|
| 2011/0290261 A1 | 12/2011 | Spainhower |
| 2013/0040266 A1 | 2/2013 | Kline |
| 2014/0087332 A1 | 3/2014 | Ueda |
| 2014/0109919 A1* | 4/2014 | Crout ................. A61F 5/56 128/861 |
| 2014/0190491 A1 | 7/2014 | Garcia |
| 2014/0373852 A1 | 12/2014 | Klein |
| 2015/0000677 A1 | 1/2015 | Magness |
| 2015/0114403 A1 | 4/2015 | Togliatti |
| 2015/0136147 A1 | 5/2015 | Lucas |
| 2015/0157491 A1 | 6/2015 | Hofmann |
| 2017/0348075 A1 | 12/2017 | Otero |
| 2018/0071134 A1 | 3/2018 | Honig |

FOREIGN PATENT DOCUMENTS

| | | |
|---|---|---|
| DE | 102013110427 A1 | 4/2015 |
| ES | 1184138 U | 5/2017 |
| JP | 04-007873 U1 | 1/1992 |
| JP | 2018519978 A | 7/2018 |
| KR | 20180116089 A | 10/2018 |

OTHER PUBLICATIONS

Total Care Dental; "Bruxism Prevention, Diagnosis and Treatment in Madison"; www.tcdmadison.com; URL: https://www.tcdmadison.com/dentalhealth/Bruxism; downloaded Feb. 13, 2019.

Walton, Mark; "VitalSleep Snoring Mouthpiece Review"; SnoringHQ.com; URL: https://snoringhq.com/other-mouthpiece-reviews/vitalsleep/; downloaded Feb. 13, 2019.

* cited by examiner

FIG. 8
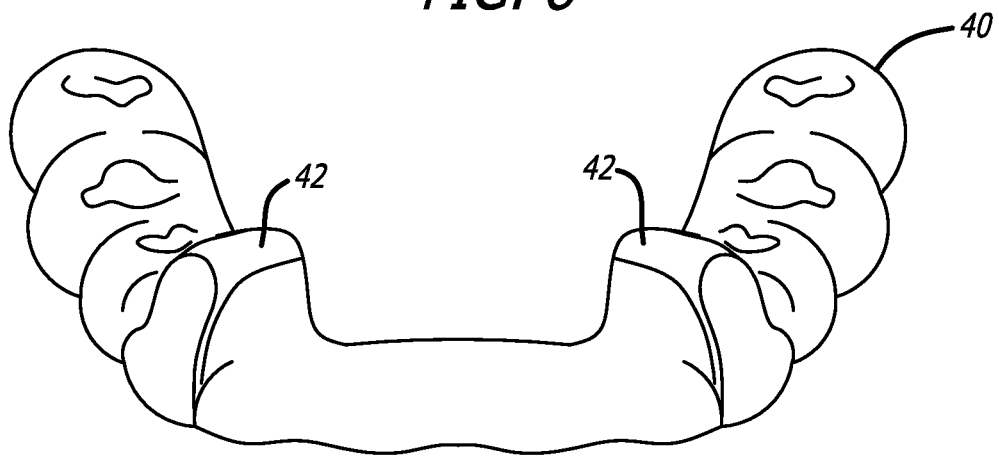
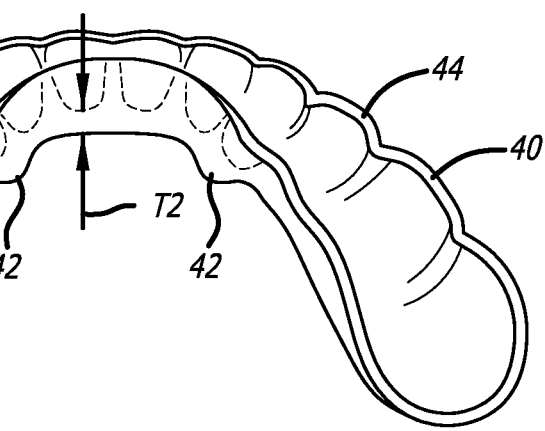
FIG. 9

DENTAL APPLIANCE

CROSS-REFERENCE TO PRIOR APPLICATIONS

This application is a continuation of and claims priority and benefit of U.S. patent application Ser. No. 16/277,663 filed Feb. 15, 2019, which issued as U.S. Pat. No. 11,369,510 on Jun. 28, 2022.

BACKGROUND

The present invention relates generally to mouth guards. More particularly, the present invention relates to a mouth guard for reducing tooth damage during sleep.

In humans, there are two dental arches: a mandibular arch (i.e., the arch of teeth along the mandible (commonly referred to as the lower jaw) or lower arch) and a maxillary arch (i.e., the arch of teeth along the maxilla (commonly referred to as the upper jaw) or upper arch). Teeth along the mandibular or lower arch are commonly referred to as 'the lower teeth,' and teeth along the maxillary arch or upper arch are commonly referred to as 'the upper teeth.'

Bruxism is excessive teeth grinding or jaw clenching. During the normal process of mastication (i.e., chewing food), one or more lower teeth come into contact with one or more upper teeth as food is masticated (i.e., chewed). Generally, during chewing, food is disposed between only a few of the lower and upper teeth. People chewing their food tend to focus on grinding the food with just those particular teeth where the food is located, and avoid needlessly grinding their other teeth together in those places where there is no food to chew. However, some people grind or clench their teeth at times other than when chewing food. Bruxism is excessive teeth grinding or jaw clenching, and it can occur during sleep. Bruxism during sleep is referred to as nocturnal bruxism. While the cause of nocturnal bruxism is not completely understood, it is likely due to various factors including, but not limited to, personality, stress, and emotion. The majority of people with nocturnal bruxism do not make noises while grinding or clenching their teeth during sleep. However, there are a number of people who do create noises (e.g., screeching noises) from grinding or clenching their teeth during sleep.

Tooth wear caused by bruxism affects the occlusal surfaces (i.e., the biting surfaces) of the teeth. The exact location and pattern of tooth wear depends on how the bruxism occurs (e.g., when the canines and incisors of the opposing mandibular and maxillary arches are moved against each other laterally, this can lead to the wearing down of the incisal edges of the teeth. People with bruxism may grind their anterior teeth (i.e., front teeth) and may also grind their posterior teeth (i.e., back teeth). Adult anterior teeth include the central and lateral incisors and the canine teeth, and make up the six upper and six lower front teeth. Adult posterior teeth include three molars and two premolars (or bicuspids) and make up the ten upper and ten lower back teeth. This grinding and clenching of teeth can apply large amounts of force on those teeth being clenched or ground together. The force of this grinding and clenching of teeth can wear away the enamel layer of one or more teeth, and expose the dentin layer of these teeth to the grinding and clenching. The dentin layer is softer and more vulnerable to wear and tooth decay than the enamel layer. If enough of the tooth is worn away or decayed, the tooth will effectively be weakened, and may fracture under the increased forces that occur in bruxism. This grinding and clenching can subsequently cause various oral health issues including, but not limited to, toothaches, cavities, periodontitis, and tooth loss.

When a person has stress and goes to sleep, that person can unconsciously use their head, neck, and shoulder muscles to contract their lower jaw so that one or more of their lower teeth (i.e., one or more teeth of the mandibular arch) come into contact with one of more of their upper teeth (i.e., one or more teeth of the maxillary arch) as their lower jaw moves in lateral and protrusive directions relative to their mouth. This, in turn, will cause lateral forces on that person's upper and lower teeth. One tooth is usually the weakest link due to the tremendous amount of lateral force applied to this particular tooth by an opposing tooth. This lateral force will cause this particular tooth to shift left and right due to the opposing tooth being stronger and unloading force that is far greater than the amount of force this particular tooth can bear. After many nights of this force being applied to this tooth particular from grinding, the person can experience various symptoms as a result of the grinding and clenching that include, but are not limited to, toothaches, cavities, periodontitis, and tooth loss.

Different types of dental appliances (e.g., mouth guards) have been proposed to protect teeth from the effects of bruxism. However, such dental appliances have their limitations and can always be improved.

Accordingly, there is a need for an improved dental appliance in the form of a mouth guard. There is also a need for a mouth guard that protects teeth from the effects of bruxism during sleep. There is an additional need for a mouth guard that is easier to manufacture, assemble, adjust, and maintain. The present invention satisfies these needs and provides other related advantages.

SUMMARY

The mouth guard assembly illustrated herein provides an improved mouth guard. The mouth guard assembly illustrated herein provides an improved mouth guard for protecting teeth from the effects of bruxism during sleep. The mouth guard assembly illustrated herein provides a mouth guard assembly that is easier to manufacture, assemble, adjust, and maintain.

In an illustrative embodiment, a mouth guard includes a tray configured to encompass at least anterior teeth of a maxillary arch. The tray includes a pair of protrusions extending away from the tray, each protrusion configured to generally overlie a portion of at least one anterior tooth of the maxillary arch. The protrusions are configured to engage at least one tooth of a mandibular arch, whereby damage to the at least anterior teeth of the maxillary arch is reduced or prevented.

In a further illustrative embodiment, the tray is configured to further encompass at least one posterior tooth of the maxillary arch.

In an additional illustrative embodiment, each protrusion is sloped on at least a palate side of the maxillary arch.

In an additional illustrative embodiment, each protrusion is sloped on at least a labial side of the maxillary arch.

In another illustrative embodiment, a mouth guard includes a tray configured to encompass at least anterior teeth of a mandibular arch. The tray includes a pair of protrusions extending away from the tray, each protrusion configured to generally overlie a portion of at least one anterior tooth of the mandibular arch. The protrusions are configured to engage at least one tooth of a maxillary arch, whereby damage to the at least anterior teeth of the mandibular arch is reduced or prevented.

In a further illustrative embodiment, the tray is configured to further encompass at least one posterior tooth of the mandibular arch.

In an additional illustrative embodiment, each protrusion is sloped on at least a palate side of the mandibular arch.

In an additional illustrative embodiment, each protrusion is sloped on at least a labial side of the mandibular arch.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The various present embodiments now will be discussed in detail with an emphasis on highlighting the advantageous features with reference to the drawings of various embodiments. The illustrated embodiments are intended to illustrate, but not to limit the invention. These drawings include the following figures, in which like numerals indicate like parts:

FIG. 8 illustrates a front, upper view of a top side of the lower mouth guard tray of FIG. 1;

FIG. 9 illustrates a rear, upper view of a bottom side of the lower mouth guard tray of FIG. 1;

DETAILED DESCRIPTION

Figure 1:
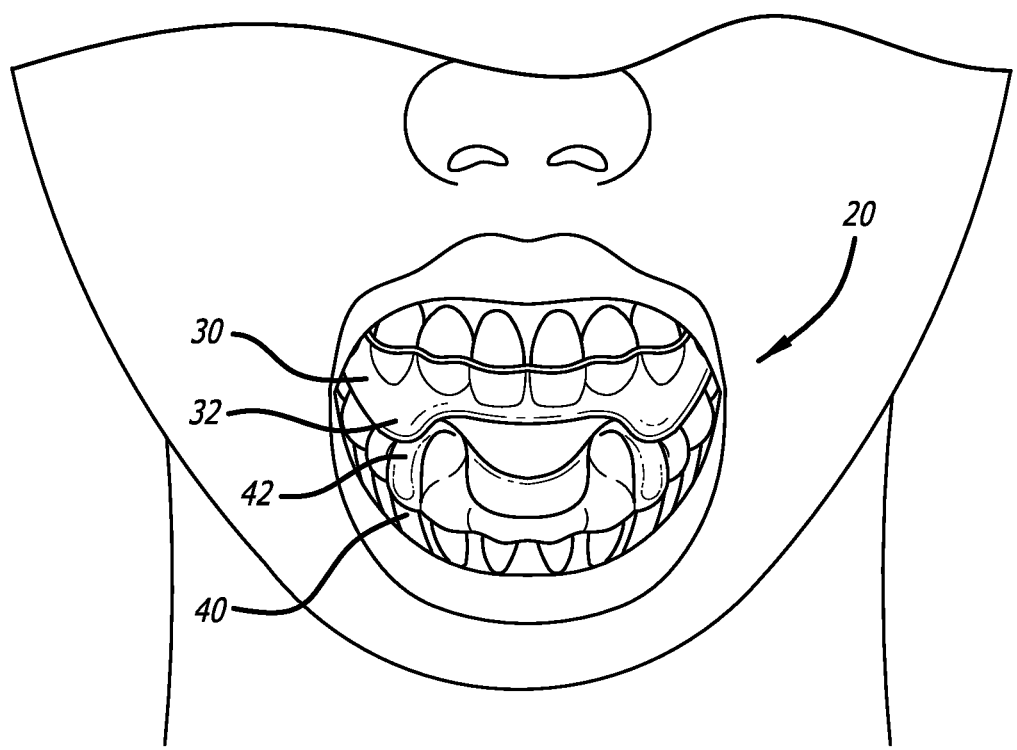
FIG. 1 illustrates a front view of a user's open mouth, with an upper mouth guard tray covering a least a portion of the user's upper teeth and a lower mouth guard tray covering at least a portion of the user's lower teeth, in accordance with an embodiment of the present invention.
Figure 2:
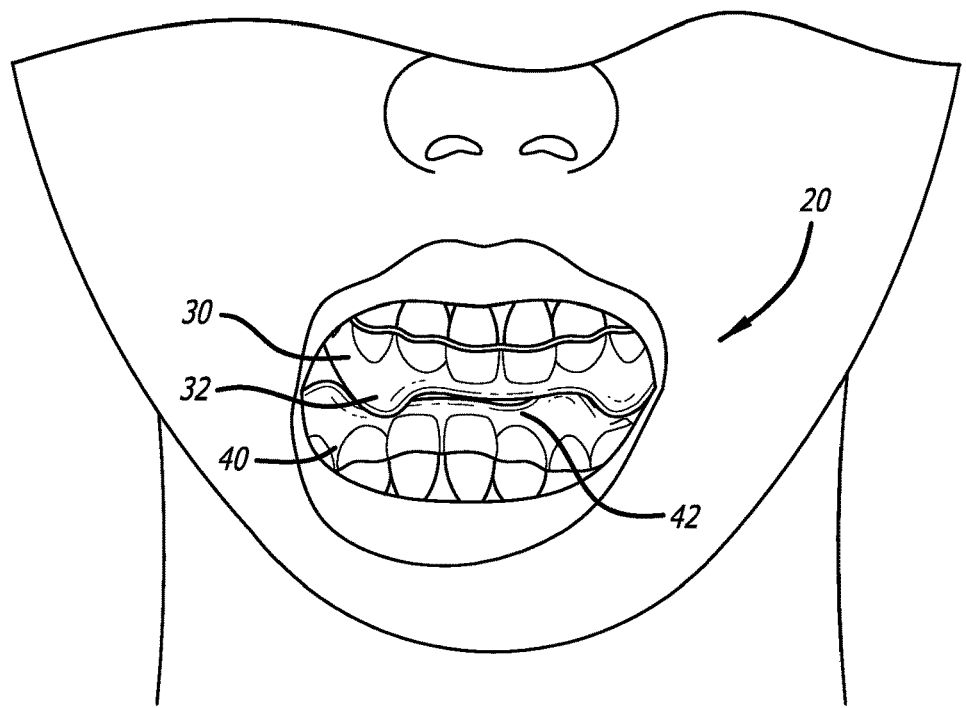
FIG. 2 illustrates the upper and lower mouth guard trays of FIG. 1, with the user's lower jaw moved laterally to the user's right as the user grinds their teeth.
Figure 3:
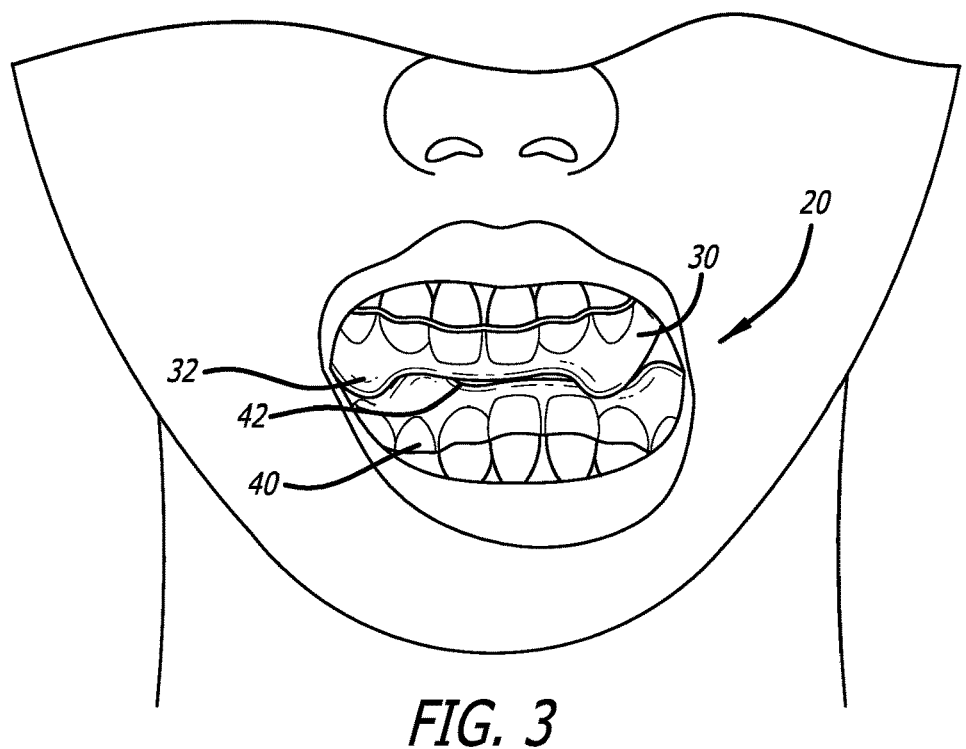
FIG. 3 illustrates the upper and lower mouth guard trays of FIG. 1, with the user's lower jaw moved laterally to the user's left as the user grinds their teeth.
Figure 4:
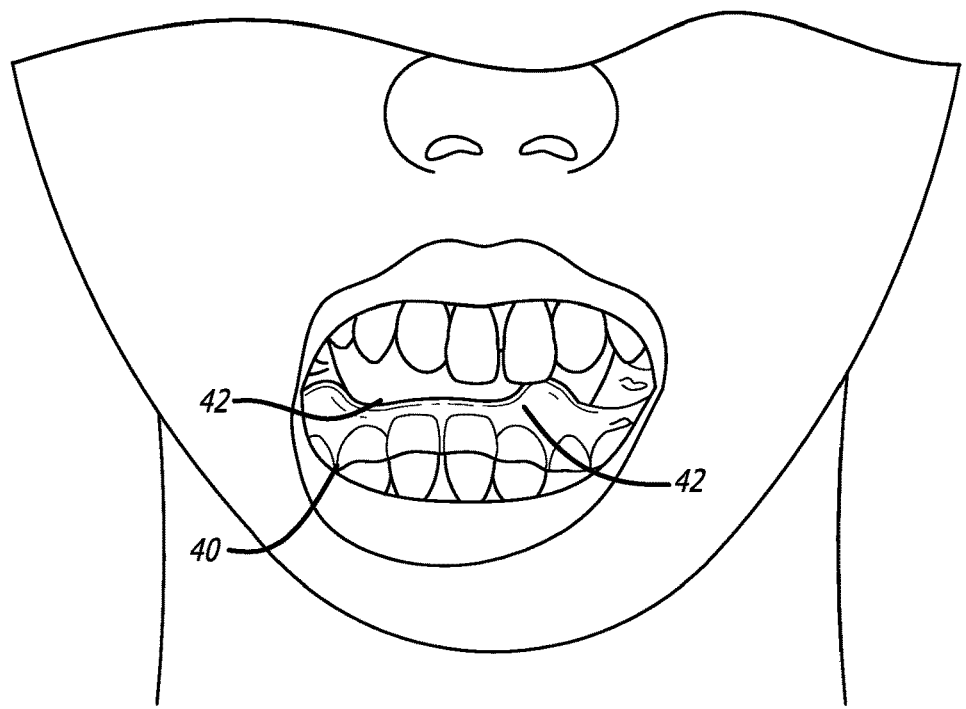
FIG. 4 illustrates the user wearing only the lower mouth guard tray of FIG. 1, with the user's lower jaw moved laterally to the user's right.
Figure 5:
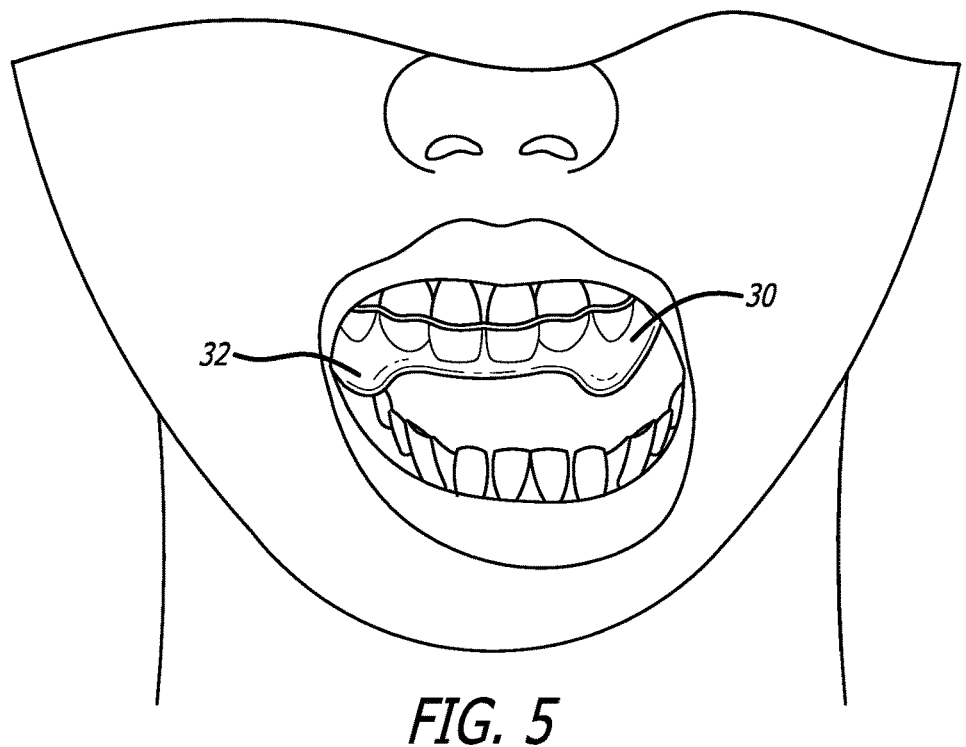
FIG. 5 illustrates the user wearing only the upper mouth guard tray of FIG. 1, with the user's lower jaw moved laterally to the user's left.
Figure 6:
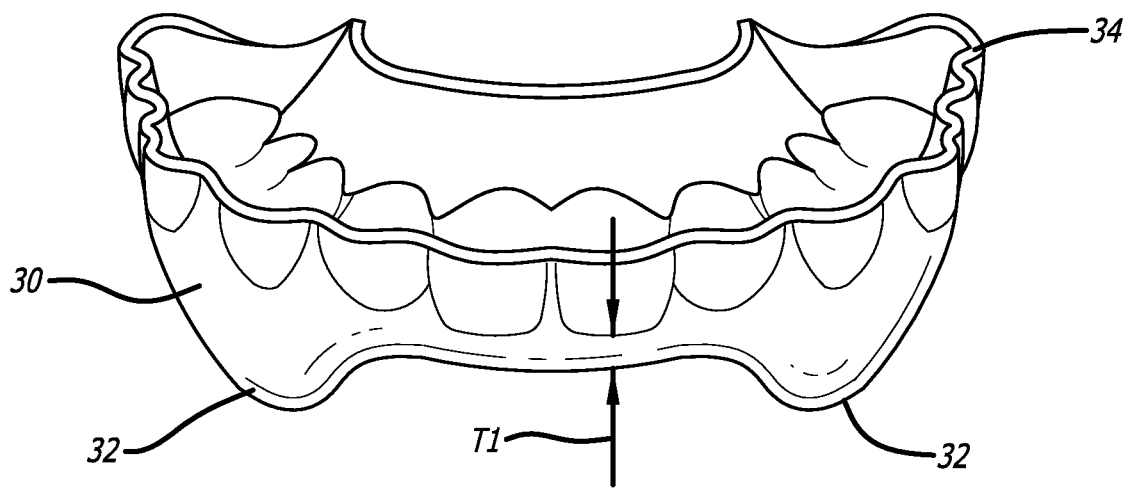
FIG. 6 illustrates a front, upper view of a top side of the upper mouth guard tray of FIG. 1.
Figure 7:
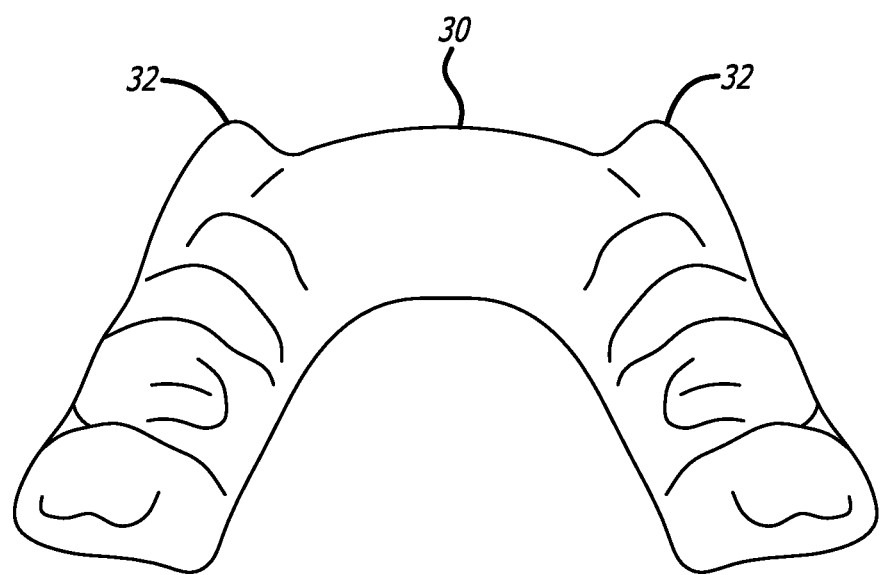
FIG. 7 illustrates a rear, upper view of a bottom side of the upper mouth guard tray of FIG. 1.

The following detailed description describes present embodiments with reference to the drawings. In the drawings, reference numbers label elements of present embodiments. These reference numbers are reproduced below in connection with the discussion of the corresponding drawing features.

It is to be understood that the figures and descriptions of the present invention have been simplified to illustrate elements that are relevant for a clear understanding of the present invention, while eliminating, for the purpose of clarity, many other elements found in mouth guards. Those of ordinary skill in the pertinent arts may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the pertinent arts.

As shown in FIGS. 1-12 for purposes of illustration, an embodiment of the present invention resides in a mouth guard assembly 20 including a mouth guard tray 30 for teeth of a user's upper dental arch (i.e., an upper guard tray 30), and a mouth guard tray 40 for teeth of a user's lower dental arch (i.e., a lower guard tray 40). Each guard tray 30, 40 is fabricated using thermoplastic polyurethane (TPU) material. An example of TPU material used to form the guard trays 30, 40 is the proprietary CLEARSPLINT brand material from Astron Dental Corporation (www.astrondental.com). The TPU material may be optically clear (i.e., generally transparent), translucent, or opaque. The TPU material may be colored or uncolored.

Both mouth guard trays 30, 40 can be worn at the same time. Alternatively, just one of the mouth guard trays 30, 40 can be worn. For example, the upper guard tray 30 can be worn on the upper arch with no mouth guard tray on the lower arch (or the lower guard tray 40 can be worn on the lower arch with no mouth guard tray on the upper arch). If worn on both dental arches or just one of the dental arches, the result will be that the teeth on both arches will be protected. If a mouth guard tray is worn on just one arch, the mouth guard tray will be designed to cover all existing teeth on that arch. The number of teeth covered will depend on the unique dentition of each individual patient. At a minimum, the mouth guards 30, 40 extend from incisors at a front of the mouth back towards, and generally covering, at least one of the premolars on each side of the patient's mouth. It is preferable that all teeth be covered by the mouth guards 30, 40 in order to distribute the grinding force. Coverage of the molars, for example, can reduce the possibility of supra-eruption of one or more of a patient's molars, especially if a patient is missing a molar on one of their dental arches that would normally oppose a molar on the other dental arch. How far back the mouth guard tray 30, 40 extends can vary from patient-to-patient, as each individual patient's dentition is unique.

Each of the mouth guards 30, 40 is designed to include a pair of protrusions 32, 42 that will generally cover an area over the user's canine teeth, but can also generally cover a lateral area extending between the user's lateral incisor, canine, and first premolar teeth. Due to the uniqueness of each individual, the protrusions 32, 42, may generally cover an area over portions of the user's lateral incisor and canine teeth, an area generally over the user's canine teeth, and an area generally over the user's canine and first premolar teeth. Placement of the protrusions 32, 42, over just the anterior teeth should be avoided as anterior teeth like the incisors have shorter roots and less periodontal ligament which makes them not as strong as the canine teeth and more vulnerable to the grinding forces. If the protrusions 32, 42 are placed over just anterior teeth such as the central incisors or lateral incisors, the force from grinding could cause these particular anterior teeth to shift outward and be more protrusive. Once the central incisors or lateral incisors are protrusive, gaps can form between the lateral incisors and the canines, and this can result in the incisors being more at risk of periodontal disease.

The protrusions 32 are configured to engage the canine or first premolar teeth of the mandibular arch; and the protrusions 32 grind against the mandibular canine or premolar tooth during a lateral excursion which is the motion when the mandible or lower jaw moves generally laterally (i.e., generally left and right) during grinding movement. The maxillary canines (or upper canines) are preferable over the other teeth is because the canines have the longest roots and can withstand the force of grinding. Also, the canine teeth are located the most distal from the temporomandibular joint (TMJ) as compared to the molars or premolars. The closer the tooth is to the TMJ, the stronger the force created by the TMJ muscles which would cause damage to the teeth. Their long root and location give the canines an advantage over the molars and premolars to withstand the force caused by the TMJ muscles during grinding or clenching.

The protrusions 32, 42 have a generally fang-like appearance. In the alternative, the protrusions 32, 42, can be shaped as desired to accommodate a particular user's unique dentition. For example, the lower portion of the protrusions 32 can have a flat-shaped bottom portion rather than a sharp fang-like bottom portion. Likewise, the upper portion of the protrusions 42 can have a flat-shaped top portion rather than a 'sharp' fang-like top portion. The flat-shaped bottom portion of the protrusions of the upper tray 30 can still function as the grinding contact point against the mandibular canines and be just as effective as the 'sharp' fang-like bottom portion of the protrusions 32. Likewise, with regard to flat-shaped top portion of the protrusions of the lower tray 40 still able to function as the grinding contact point against the maxillary canines and be just as effective as the 'sharp' fang-like top portion of the protrusions 42.

The angle of the slope of the protrusions 32, 42 also varies from zero (0) degrees of a flat top to as much as seventy-five (75) degrees that mimics the anatomy of a canine. This angle is determined by the lateral movement of the jaw and hence the mandibular anterior teeth and posterior teeth do not come into contact with the maxillary mouth guard 30 during the grinding movement.

Figure 10:
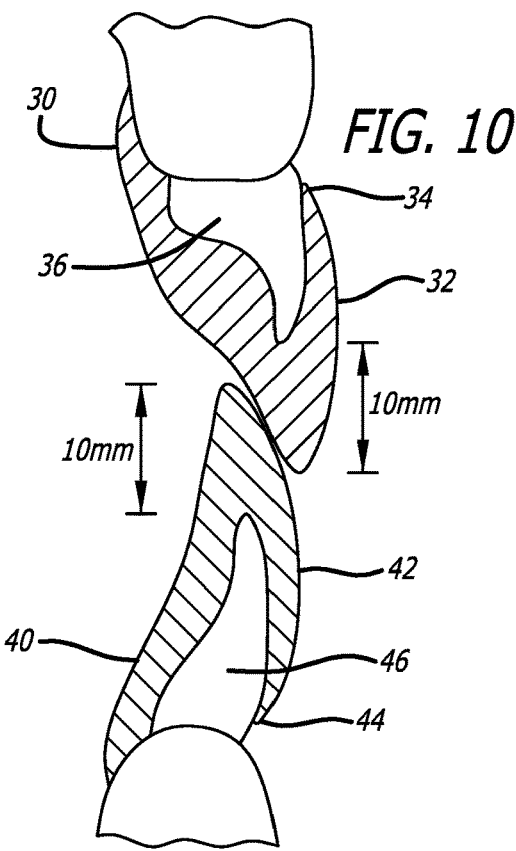
FIG. 10 illustrates a section view illustrating contact between the protrusions of the upper and lower mouth guard trays during grinding.
Figure 11:
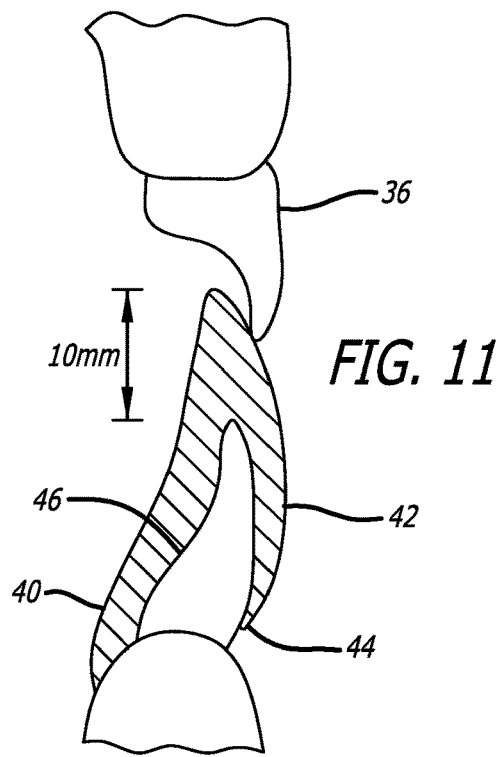
FIG. 11 illustrates a section view illustrating contact between the protrusion of the lower mouth guard tray with upper dentition during grinding.
Figure 12:
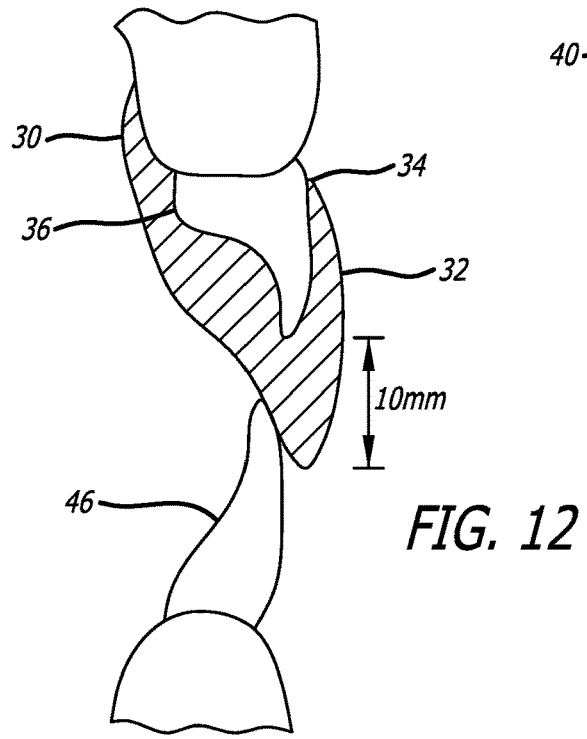
FIG. 12 illustrates a section view illustrating contact between the protrusion of the upper mouth guard tray with lower dentition during grinding.

Due to the uniqueness of each individual's dentition, the length of the protrusions 32, 42 may vary from person-to-person from five millimeters to twenty millimeters (5 mm to 20 mm) but the most optimal length is generally ten millimeters (10 mm). For example, when the length of the protrusion 32 is too short, the lower posterior teeth, such as the mandibular second premolars and the molars, can still come into contact with the mouth guard 30 during the lateral excursion of grinding. If the protrusion 32 is too long, the protrusion 32 may fracture during grinding. The other areas of the mouth guard 30 have to be thin to avoid contact with the mandibular teeth to prevent damage to the anterior teeth and the posterior teeth. As seen in FIGS. 10-12, the protrusions 32, 42 are generally ten millimeters (10 mm) thick along a longitudinal length from a coronal portion of the dentition to a coronal portion of the protrusion 32, 42. For example, as seen in FIG. 10, with the patient wearing both upper and lower mouth guards 30, 40, the protrusion 32 can be generally ten millimeters (10 mm) long from the tip of one of the user's teeth (e.g., canine tooth) 36 on the maxillary arch, and the protrusion 42 can be generally ten millimeters (10 mm) long from the tip of one of the user's teeth (e.g., lateral incisor) 46 on the mandibular arch, with sloped portions of the protrusions 32, 42 deflecting each other. In this particular instance, the protrusions 32, 42 of the mouth guards 30, 40 can be seen contacting each other along their respective ten millimeter (10 mm) lengths. However, the protrusions 32, 42 may contact each other or other portions of their opposing mouth guards at any number of places. In FIG. 11, an example shows the patient wearing only a lower mouth guard tray 40, with the protrusion 42 being generally ten millimeters (10 mm) long from the tip of one of the user's teeth (e.g., lateral incisor) 46 on the mandibular arch, and the protrusion 42 contacting one of the user's teeth (e.g., canine tooth) 36 on the maxillary arch. In FIG. 12, an example shows the patient wearing only an upper mouth guard tray 30, with the protrusion 32 being generally ten millimeters (10 mm) long from the tip of one of the user's teeth (e.g., canine) 36 on the maxillary arch, and the protrusion 32 contacting one of the user's teeth (e.g., lateral incisor) 46 on the mandibular arch. Ten millimeters (10 mm) is about the minimum distance necessary between the maxillary and mandibular dentitions. Two millimeters (2 mm) is about the minimum thickness T1 of the material of the upper mouth guard tray 30 between the central incisor and a bottom side of the upper mouth guard tray 30 that contacts the lower mouth guard tray 40. As each individual is unique, the thickness T1 of the upper mouth guard tray 30 between the central incisor and the bottom side of the upper mouth guard tray 30 can vary from individual-to-individual. Likewise, two millimeters (2 mm) is about the minimum thickness T2 of the material of the lower mouth guard tray 40 between the central incisor and a top side of the lower mouth guard tray 40 that contacts the upper mouth guard tray 30. As each individual is unique, the thickness T2 of the lower mouth guard tray 40 between the central incisor and the top side of the lower mouth guard tray 40 can vary from individual-to-individual. The anterior and posterior dentition area on the mouth guard trays 30, 40 will be minimal where opposing dentition will not come into contact with these two areas. Because of the protrusions 32, 42, the anterior and posterior dentitions will not be under direct force during grinding or clenching. Each protrusion 32, 42 includes a curved slope on a palate side of the protrusion 32, 42 that creates a gap between the upper and lower dentition when the user is grinding generally laterally (i.e., sideways). Each protrusion 32, 42 includes a curved slope on a labial side of the protrusion 32, 42. In the alternative, the slopes on the palate and labial sides of the protrusions 32, 42 may be angular, or a combination of angular and curved. The shape of the protrusions 32, 42 generally mimic the anatomy of a canine tooth, but the slopes on the palate and labial sides of the protrusions 32, 42 may be shaped as needed in order to accommodate the unique dentition of a particular user. The protrusions 32, 42 prevent the anterior teeth and molars from coming into contact during lateral excursions caused by grinding by guiding the guard trays 30, 40 away from each other and cushioning contact between the guard trays 30, 40. Wherever the guard trays 30, 40 come into contact, the TPU material provides cushioning and dissipation of the grinding force.

During lateral excursions or lateral movements of the lower jaw while the user grinds their teeth during sleep, the protrusions 32, 42 will cause the distance between the anterior and posterior maxillary and mandibular teeth to increase. Because of this increase, the anterior and posterior teeth will not be in direct contact and, hence, the force exerted on these teeth will be diminished; prolonging the life of these teeth. As for the canines and premolars covered by the protrusions 32, 42, the ten millimeter (10 mm) thickness will also lessen the force applied directly to these teeth. As the distance between both arches increases, the effect of the force exerted by muscles in the user's head, neck, and shoulder will be diminished. The canine teeth are the longest teeth in both arches of dentitions and the canines also have more periodontal fibers which can tolerate more force than can be tolerated by the anterior incisors during grinding. As for the molars in the posterior region, the force on the molars from grinding is many times more than the force on the canines, premolars, and incisors, because the molars are closer to the temporomandibular (TMJ) joint.

A first method for fabricating the upper and lower guards 30, 40 is for a dentist or other dental professional to take impressions of the patient's upper and lower arches of dentition, as well as a bite registration, and then send them to a dental laboratory. In the alternative, an impression can be taken of just one of the arches of dentition if it is determined that a mouth guard is required for only one of the arches of dentition. At the dental laboratory, models of the patient's upper and lower arches of dentition are made from the impressions. A technician at the dental laboratory then heats up a sheet of TPU material with a heating machine to make a guard tray. This sheet of TPU material softens and can be formed around a selected one of the models of the patient's dentition (e.g., the upper arch of dentition). While the material is still soft, the technician cuts and shapes the material to forms the upper mouth guard tray 30 and protrusions 32. This process is repeated to create the lower mouth guard tray 40 and protrusions 42. The protrusions 32, 42 are shaped such that each protrusion 32, 42 is sloped on palate and labial sides of the maxillary and mandibular arches. As the dentition of each individual is unique, the protrusions 32, 42 are sloped to meet the unique needs of each individual. The technician would use the models of the patient's upper and lower arches of dentition to generally match the slope of the protrusions 32, 42 to the natural slope(s) of the patient's canines, incisors and/or bicuspids. Again, the unique nature of each individual's dentition is taken into account. An upper rim 34 of the upper mouth guard tray 30 should extend at least halfway up the coronal portion of the teeth but should not extend above the patient's gumline. Likewise, a lower rim 44 of the lower mouth guard tray 40 should extend at least halfway down the coronal portion of the teeth but should not extend below the patient's gumline. An alternative method is for a pre-fabricated mouth guard made of TPU material that can be softened by boiling water and shaped around the upper and lower arches of dentition. In a further alternative, if a dental CAD/CAM machine is used, guard trays 30, 40 can be created by a digital impression of a patient's dentition being taken, and then using the CAD/CAM machine to form the guard trays 30, 40.

The TPU material of the mouth guard trays 30, 40 is hard enough to prevent contact between the upper and lower dentitions as the guards 30, 40 come into contact with each other when grinding starts. Sometimes an individual sleeps with their mouth open, and their upper and lower dentition will come into contact when grinding starts. For example, once the mouth guard trays 30, 40 and dentitions come into contact, the hardness of the TPU material of the mouth guard trays 30, 40 prevents the opposing dentitions from coming into direct contact, and decreasing the effect of the grinding or clenching force from muscles in the patient's head, neck, and/or shoulders. Using a soft material (i.e., a material softer than TPU) will not be as effective as a patient might be able to "bite through" material softer than TPU when the upper and lower dentitions bear down against the mouth guard trays 30, 40 (i.e., mouth guard trays made of material softer than TPU) at first contact between the upper and lower guard trays 30, 40 when grinding starts, or even if the upper and/or lower dentition does not break through the soft material during grinding, the soft material is no more effective than a stick of well-chewed chewing gum at dissipating the force on one or more teeth from the contact of opposing dentition during grinding and clenching.

By wearing the mouth guard tray 30, 40 during grinding and clenching, the force from head, neck, and shoulder muscles would be diminished. Hence, there is less damage on the periodontal fibers and the life of each individual dentition is prolonged. When there is less force applied to these periodontal fibers, there will be less toothaches, cavities, periodontitis, and tooth loss.

In use, a user places the mouth guard trays 30, 40 on the lower and upper arches of their mouth prior to going to sleep at night. During the protrusive movement of the lower jaw, moving the lower jaw forward and back while applying forces on the incisors and anterior dentition, the protrusions 32, 42 will also cause the anterior dentitions on both the upper and lower arches not to directly contact which would alleviate the forces caused by grinding or clenching.

As disclosed above, the mouth guard trays 30, 40 can be used at the same time. Alternatively, each mouth guard tray 30, 40, can be used without the other. In any event, the function of each mouth guard tray 30, 40 is unchanged if used alone or together (although the number of covered teeth may vary due to the unique nature of each individual's dentition).

Throughout the specification, it is to be understood that the term "opposing" refers to the opposing arch which is not covered by the mouth guard tray 30, 40. For example, in the context of the upper guard tray 30, the term "opposing arch" refers to the mandibular arch when the upper guard tray 30 is placed over teeth of the maxillary arch. In another example, in the context of the lower guard tray 40, the term "opposing arch" refers to the maxillary arch when the lower guard tray 40 is placed over teeth of the mandibular arch.

Although the present invention has been discussed above in connection with use in a human mouth, the present invention is not limited to that environment and may also be used in the mouths of other species.

In addition, the claimed invention is not limited in size and may be constructed in miniature versions or for use in very large-scale applications in which the same or similar principles of motion and friction control as described above would apply. Likewise, the length and width of the mouth guard are not to be construed as drawn to scale, and that the lengths/widths of the mouth guard may be adjusted in conformance with the area available for its placement as the dimensions of a human mouth may vary from individual to individual. Furthermore, the figures (and various components shown therein) of the specification are not to be construed as drawn to scale.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the disclosure to achieve one or more of the desired objects or results.

The numerical values mentioned for the various physical parameters, dimensions or quantities are only approximations and it is envisaged that the values higher/lower than the numerical values assigned to the parameters, dimensions or quantities fall within the scope of the disclosure, unless there is a statement in the specification specific to the contrary.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Spatially relative terms, such as "front," "rear," "left," "right," "inner," "outer," "beneath", "below", "lower", "above", "upper," "horizontal," "vertical" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The above description presents the best mode contemplated for carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above that are fully equivalent. Consequently, this invention is not limited to the particular embodiments disclosed. On the contrary, this invention covers all modifications and alternate constructions coming within the spirit and scope of the invention as generally expressed by the following claims, which particularly point out and distinctly claim the subject matter of the invention.

What is claimed is:

1. A mouth guard, comprising:
   a tray configured to encompass at least anterior teeth of a maxillary arch;
   wherein the tray includes a pair of protrusions extending away from the tray, each protrusion configured to generally overlie a portion of at least one anterior tooth of the maxillary arch; and wherein each protrusion is configured to be about five millimeters to about twenty millimeters along a longitudinal length from a coronal portion of the at least one anterior tooth of the maxillary arch to a coronal portion of the protrusion;
   whereby the protrusions are configured to engage at least one tooth of a mandibular arch; and
   whereby damage to the at least anterior teeth of the maxillary arch is reduced or prevented.

2. The mouth guard of claim 1, wherein the tray is configured to further encompass at least one posterior tooth of the maxillary arch.

3. The mouth guard of claim 1, wherein each protrusion is sloped on at least a palate side of the maxillary arch.

4. The mouth guard of claim 1, wherein each protrusion is sloped on at least a labial side of the maxillary arch.

5. The mouth guard of claim 1, wherein each protrusion is configured to engage at least two teeth of a mandibular arch.

6. The mouth guard of claim 1, wherein each protrusion is configured to be about ten millimeters along a longitudinal length from a coronal portion of the at least one anterior tooth of the maxillary arch to a coronal portion of the protrusion.

7. The mouth guard of claim 1, wherein each protrusion is configured to include a fang shaped distal end.

8. A mouth guard, comprising:
   a tray configured to encompass at least anterior teeth of a mandibular arch;
   wherein the tray includes a pair of protrusions extending away from the tray, each protrusion configured to generally overlie a portion of at least one anterior tooth of the mandibular arch; and wherein each protrusion is configured to be about five millimeters to about twenty millimeters along a longitudinal length from a coronal portion of the at least one anterior tooth of the mandibular arch to a coronal portion of the protrusion;
   whereby the protrusions are configured to engage at least one tooth of a maxillary arch; and
   whereby damage to the at least anterior teeth of the mandibular arch is reduced or prevented.

9. The mouth guard of claim 8, wherein the tray is configured to further encompass at least one posterior tooth of the mandibular arch.

10. The mouth guard of claim 8, wherein each protrusion is sloped on at least a palate side of the mandibular arch.

11. The mouth guard of claim 8, wherein each protrusion is sloped on at least a labial side of the mandibular arch.

12. The mouth guard of claim 8, wherein each protrusion is configured to engage at least two teeth of a maxillary arch.

13. The mouth guard of claim 8 wherein each protrusion is configured to be about ten millimeters along a longitudinal length from a coronal portion of the at least one anterior tooth of the mandibular arch to a coronal portion of the protrusion.

14. The mouth guard of claim 8, wherein each protrusion is configured to include a fang shaped distal end.

* * * * *